United States Patent

Cimber

Patent Number: 5,676,647
Date of Patent: Oct. 14, 1997

[54] TAMPON APPLICATOR

[76] Inventor: Hugo Cimber, Bernstrasse 34, 3072 Ostermundigen, Switzerland

[21] Appl. No.: 668,995
[22] Filed: Jun. 21, 1996

[30] Foreign Application Priority Data

Jun. 22, 1995 [CH] Switzerland ............... 1832/95

[51] Int. Cl.$^6$ ............... A61F 13/20; A61K 9/02
[52] U.S. Cl. ............... 604/11; 604/12; 604/14; 604/15; 604/288
[58] Field of Search ............... 604/11–18, 285, 604/286, 288, 363, 904

[56] References Cited

FOREIGN PATENT DOCUMENTS

| 3248152 | 6/1984 | Germany | 604/14 |
|---|---|---|---|
| 753294 | 7/1956 | United Kingdom | 604/904 |

Primary Examiner—John G. Weiss
Assistant Examiner—Dennis Ruhl
Attorney, Agent, or Firm—Townsend and Townsend and Crew LLP

[57] ABSTRACT

A tampon applicator including an insertion tube for accepting a tampon and a discharge tube for discharging the tampon. The discharge tube is displaceable in the insertion tube. Placeable upon the end area of the insertion tube on the insertion side is a container containing a therapeutic or prophylactic medicinal substance. This container is sealed off from the insertion tube by means of a foil. Provided in the insertion tube between an accepted tampon and the foil are pivotable flaps having a sharp-edged projection, and which are pivoted during insertion of the tampon by means of the forward movement of the tampon against the foil and which break through the foil with their sharp-edged projection.

8 Claims, 3 Drawing Sheets

TAMPON APPLICATOR

BACKGROUND OF THE INVENTION

Technical Field

This invention relates to a tampon applicator for insertion of a tampon.

DESCRIPTION OF THE PRIOR ART

Tampon applicators are well known in the art. German published patent application DE-A-32 48 152 discloses a tampon applicator in which a closed chamber is disposed in the insertion tube in front of the tip of the tampon. This can be achieved, for example, by attaching or screwing on an additional container filled with a medicinal substance. The chamber formed by the container is closed off with a foil adjacent towards the insertion tube.

To allow the medicinal substance in the container to come into contact with the tampon in the insertion tube, which is supposed to take place just before or during insertion of the tampon into the vagina, the container's foil, turned toward the tip of the tampon, must be broken. This can be achieved, on the one hand, through relative displacement of the container with respect to the insertion tube, the foil being broken by the insertion tube, or, on the other hand, by advancement of the tampon through the discharge tube during insertion. In especially the latter situation, the foil can only have a weak resistance to tearing since the soft surface of the tampon would not be able to push through it. It is therefore foreseen that the foil be pre-stamped or scored.

The drawback of the aforementioned invention is that the foil separating the tampon can be broken as a result of an unintentional displacement of the container, or respectively the chamber, with respect to the insertion tube. A further drawback is that the foil has to be designed to be weak so it can be broken by the forward pushing movement of the tampon and by the tampon itself. Here there is the risk that this foil can be already broken before use of the tampon applicator or before the container is placed on the insertion tube as a result of a minimal mechanical influence. As a consequently the substance in the container can leak out or, at the least the chamber will no longer be air-tight.

SUMMARY OF THE INVENTION

The object of the present invention is to create a tampon applicator including a container closed off with a foil on the area turned toward the insertion tube, the mechanical resistance to unintentional breakage of the foil being sufficiently great, but the foil nevertheless being able to be broken by the forward pushing of the tampon contained in the insertion tube through the discharge tube during insertion of the tampon in the vagina.

This object is attained, according to the invention, with a tampon applicator comprising:

an insertion tube for accepting a tampon;

a discharge tube, displaceable in the insertion tube, for discharging the tampon;

receiving elements disposed on the end area of the insertion tube on the insertion side;

a container containing a medicinal substance and having a wall, which container can be fitted into the receiving elements of the insertion tube, and which is sealed off with a cap on the outer face and with a foil on the face turned toward the insertion tube, means provided in the insertion tube for breaking through the foil, the means being disposed between the accepted tampon and the foil-sealed container placed upon the insertion tube, which means can be pushed against the foil by means of the forward movement of the tampon with the discharge tube and which means break said foil.

In a preferred embodiment, the means to break the foil consist of pivotable flaps which are pivotably fastened on the inside surface of the insertion tube and which have sharp-edged projections or pointed teeth.

Another preferred embodiment of the invention consists of having the insertion tube and the pivotable flaps made in one piece, preferably of plastic, and the pivotable connection between the flaps and the insertion tube designed as an articulated sheet or foil. The insertion tube is thus manufactured simply and inexpensively.

A further preferred embodiment of the invention includes the acceptance means for the container consisting of a cylindrical area formed on the insertion tube into which the container is insertable. For this purpose a shoulder is provided which serves as a limit stop for the inserted container, with snap means being provided which hold the inserted container against the limit stop. Because of this, the container cannot be inserted too far into the insertion tube, thereby avoiding a premature breaking of the foil.

To achieve a problem-free discharge of the tampon from the insertion tube and passage through the inserted container, the inner diameter of the insertion tube and the inner diameter of the container are essentially the same.

An embodiment of the tampon applicator according to the invention will be more fully explained in the following, by way of example, with reference to the accompanying figures.

DETAILED DESCRIPTION OF THE PREFERRED EXEMPLARY

Figure 1:
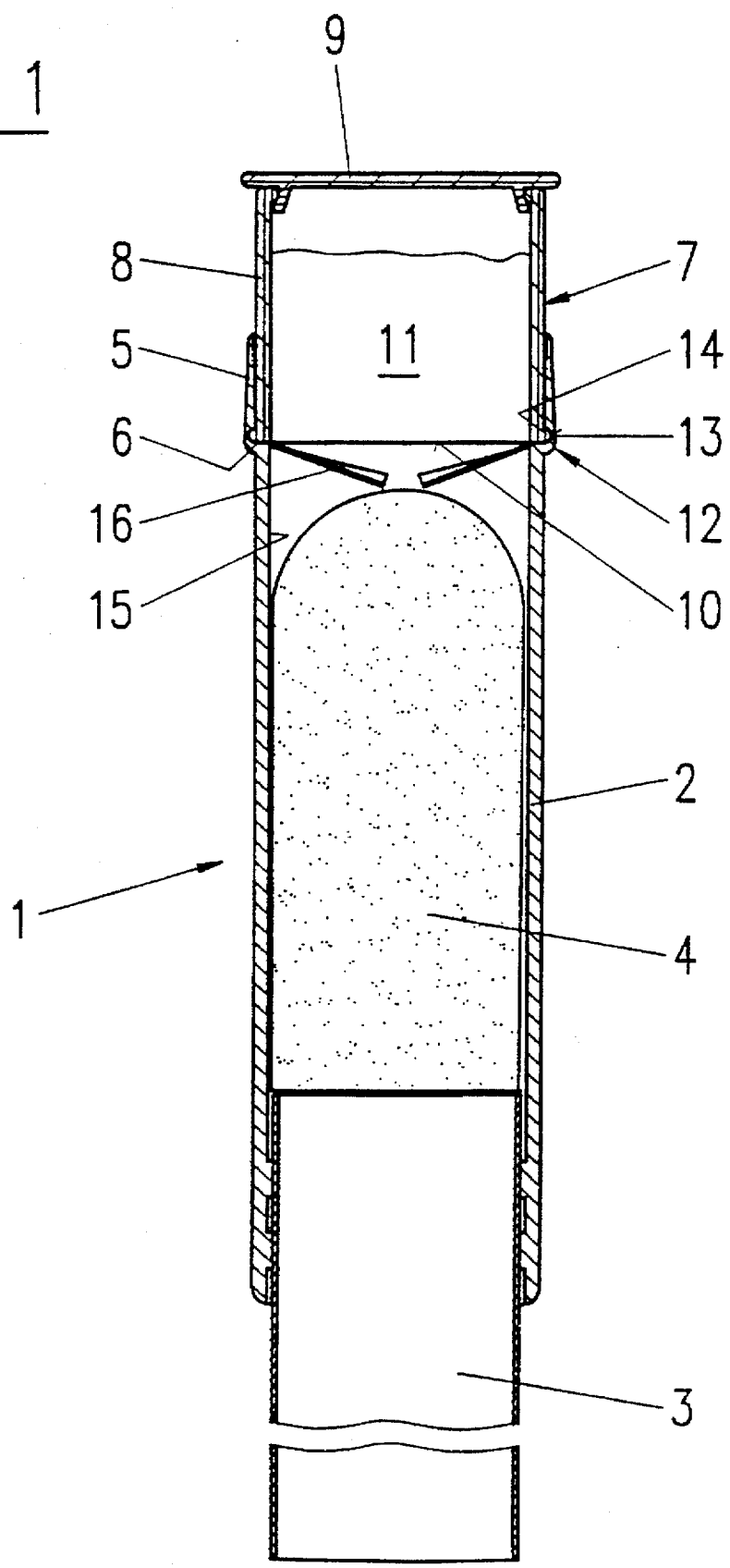
FIG. 1 is a longitudinal sectional view of a tampon applicator according to the invention with a tampon inserted therein.

With references to FIG. 1, a tampon applicator, according to the present invention comprises a hollow-cylindrical insertion tube 2 in which a discharge tube 3 is displaceably disposed. A tampon 4 is inserted into the insertion tube.

A cylindrical area 5 is formed on the side of the insertion tube 2 opposite the discharge tube 3. Since this cylindrical area 5 has a slightly larger diameter than the insertion tube 2, a shoulder 6 results.

A container 7, having a wall 8 and a removable lid 9, can be inserted into the cylindrical area 5. The container 7 is closed off with a foil toward the insertion tube 2. Contained in the container 7 is a therapeutic or prophylactic medicinal substance 11.

The container 7 is pushed into the cylindrical area 5 until it abuts the shoulder 6. The container 7 is held in this position by snap means 12 which consist of a groove 13 made on the inside in the cylindrical area 5 into which bulges 14 provided on the container 7 can be snapped. In this state, the container 7 and the insertion tube 2 are relatively firmly connected together.

Disposed on the inside surface 15 of the insertion tube 2 are pivotable flaps 16, which, in the initial position shown in FIG. 1, are essentially inwardly directed, sticking out from the inside surface 15. The insertion tube 2 and the flaps 16 can be made in one manufacturing step of the same material, preferably plastic such as polyethylene or a similar material. The pivotable connection between flap 16 and insertion tube 2 is designed as an articulated sheet or foil.

Figure 2:
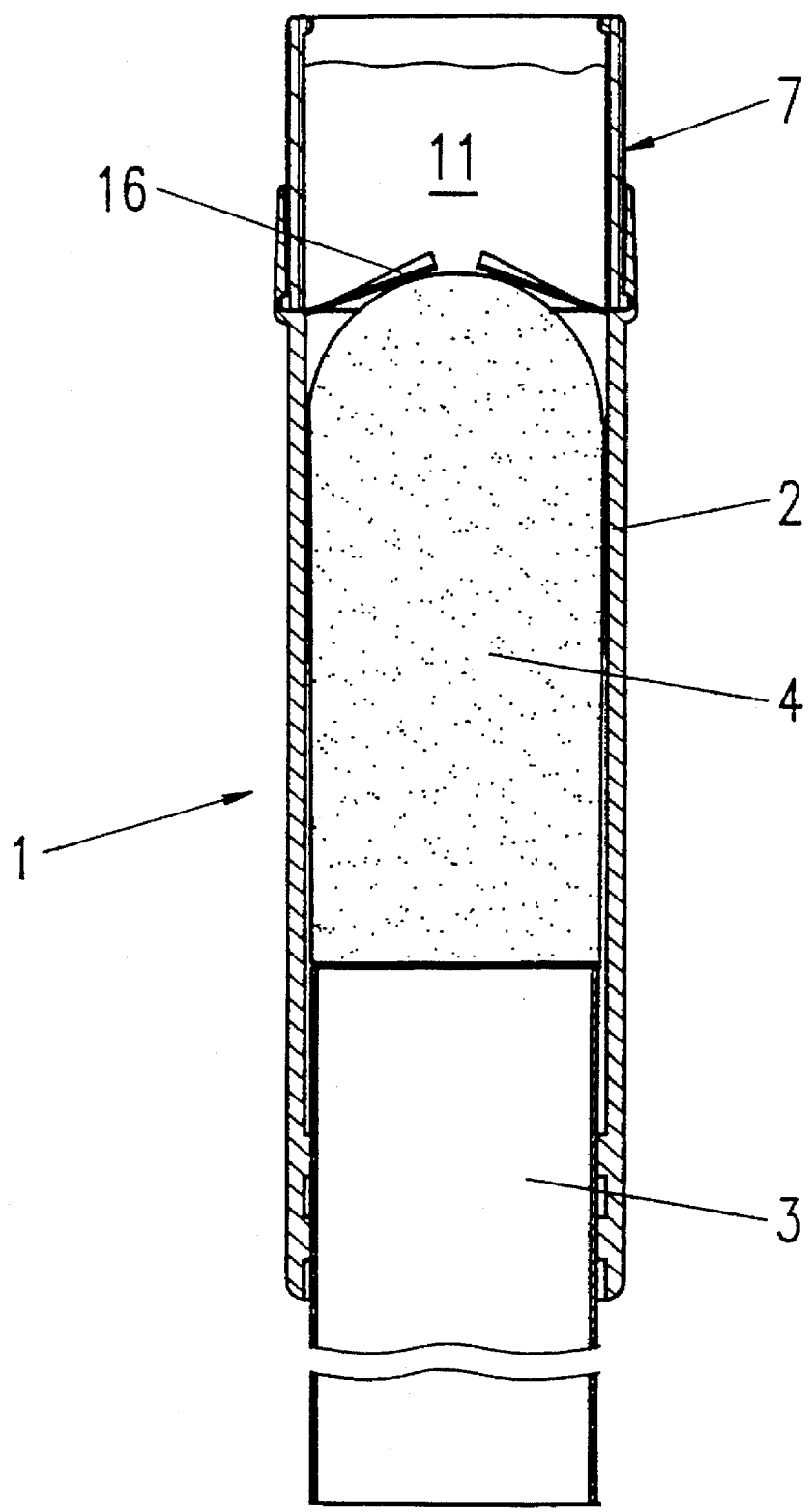
FIG. 2 is a sectional view of the tampon applicator according to FIG. 1, the tampon having been pushed forward and the foil of the container broken.

With reference to FIG. 2, to insert the tampon applicator into the vagina, the lid 9 is removed. The tampon 4 is pushed through the discharge tube 3 toward the container 7, the flaps 16 being pivoted against foil 10. The sharp-edged projection 17 (FIG. 4) breaks open the foil. The tampon 4 can be pushed further forward, and is discharged from the tampon applicator 1 with the medicinal substance 11. This discharge of the tampon 4 with the medicinal substance 11 is made easier by the fact that the inner diameter of the insertion tube 2 and the inner diameter of the container 1 are equal.

Of course all the edges of the insertion tube 2 and the container 7 are rounded so that injuries during insertion into the vagina are avoided.

Figure 3:
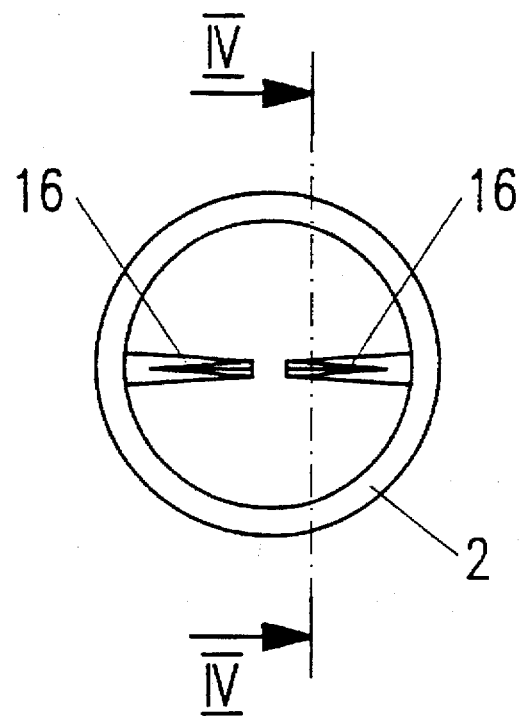
FIG. 3 is a plan view of the insertion tube according to FIGS. 1 and 2 with pivotable flaps.

Visible in FIG. 3 is the arrangement of the pivotable flaps 16 in the insertion tube 2. Two flaps 16 are provided in this embodiment, but a larger number is also conceivable.

Figure 4:
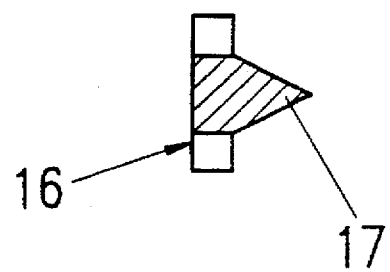
FIG. 4 is a sectional view of a flap along line IV—IV according to FIG. 3.

With reference to FIG. 4, one flap 16 is shown provided with a sharp-edged projection 17 which is directed toward the foil 10 of the container, wherein the foil is about to be broken open.

Achieved with this inventive tampon applicator is simple and secure handling, the foil 10 being designed in such a way that it is strong enough so it cannot be broken owing to unintended mechanical influences, but nevertheless can be broken by the advancement of the tampon which is to be inserted.

What is claimed is:

1. A tampon applicator comprising:
   an insertion tube for accepting a tampon;
   a discharge tube, displaceable in a first end of said insertion tube for discharging said accepted tampon;
   receiving elements disposed on an end area of the insertion tube, opposite said first end;
   a container containing a medicinal substance and having a wall, said container releasably fitted into the receiving elements of the insertion tube, and said container sealed off with a cap on an outer face and with a foil on a face opposite said cap; and
   means provided in the insertion tube for breaking through said foil, said breaking means being disposed between said first end of said insertion tube and said receiving elements, said breaking means adapted to be pushed against said foil by the forward movement of said accepted tampon with the discharge tube whereby said foil is caused to be broken open by said breaking means.

2. The tampon applicator of claim 1, wherein the means to break through the foil of the container is at least one pivotable flap which is mounted on an inside surface of the insertion tube.

3. The tampon applicator of claim 2, wherein the insertion tube and the at least one pivotable flap are made in one piece, the pivotable connection between the flap and the insertion tube being designed as an articulated sheet or foil.

4. The tampon applicator of claim 2, wherein two flaps are provided opposite each other.

5. The tampon applicator of claim 4, wherein at least one sharp-edged projection is provided on each flap whereby said projection causes said foil to be broken open when pushed against said foil.

6. The tampon applicator of claim 1, wherein the receiving elements for the container comprise a cylindrical area formed on the insertion tube into which the container can be fitted.

7. The tampon applicator of claim 6, wherein the cylindrical area is provided with a shoulder adjacent the insertion tube, which serves as a limit stop, and wherein snap means are provided which hold the inserted container.

8. The tampon applicator according to claim 6, wherein an inner diameter of the insertion tube and an inner diameter of the container are essentially equal.

* * * * *